United States Patent
Goto et al.

(10) Patent No.: US 6,642,050 B1
(45) Date of Patent: Nov. 4, 2003

(54) THREE-DIMENSIONAL CELL CULTURE MATERIAL HAVING SUGAR POLYMER CONTAINING CELL RECOGNITION SUGAR CHAIN

(75) Inventors: Mitsuaki Goto, Kawasaki (JP); Toshihiro Akaike, Nishitokyo (JP); Jun Yang, Sagamihara (JP)

(73) Assignee: Amcite Research, Ltd., Kanagawa-ken (JP)

( * ) Notice: Subject to any disclaimer, the term of this patent is extended or adjusted under 35 U.S.C. 154(b) by 0 days.

(21) Appl. No.: 09/787,239

(22) PCT Filed: Nov. 10, 1999

(86) PCT No.: PCT/JP99/06248

§ 371 (c)(1), (2), (4) Date: Mar. 16, 2001

(87) PCT Pub. No.: WO01/07582

PCT Pub. Date: Feb. 1, 2001

(30) Foreign Application Priority Data

Jul. 28, 1999 (JP) .............................. 11-213465

(51) Int. Cl.⁷ ............................ C12N 5/06; C12N 5/08; C12N 11/10
(52) U.S. Cl. ..................... 435/395; 424/93.7; 435/178; 435/325; 435/397
(58) Field of Search .................... 424/93.7; 435/177, 435/178, 325, 395, 397

(56) References Cited

U.S. PATENT DOCUMENTS 5,702,818 A * 12/1997 Cahalan et al. ............. 428/409

FOREIGN PATENT DOCUMENTS

| EP | 0 341 745 | 11/1989 |
|---|---|---|
| EP | 0 358 506 | 3/1990 |
| JP | 2-131578 | 5/1990 |
| WO | 85/01743 | 4/1985 |
| WO | 93/09176 | 5/1993 |
| WO | 93/16176 | 8/1993 |
| WO | 97/45532 | 12/1997 |
| WO | 98/56897 | 12/1998 |
| WO | 00/16818 | 3/2000 |

OTHER PUBLICATIONS

X. Chen et al., "Enzymatic and chemoenzymatic approaches to synthesis of sugar–based polymer and hydrogels", Carbohydrate Polymers, vol. 28, No. 1, 1995, pp. 15–21.

J. Rowley et al., "Alginate hydrogels as synthetic extracellular matrix materials", Biomaterials, vol. 20, No. 1, Jan. 1, 1999, pp. 45–53.

O. Smidsrød et al., "Alginate as immobilization matrix for cells", Trends in Biotechnology, vol. 8, No. 3, Mar. 1, 1990, pp. 71–78.

F. Corelli et al., "Synthesis of Bicyclo[9.3.1]pentadecane Derivatives, Interesting Intermediates for the Preparation of Taxuspine U and Related Diterpenoids[1]", Tetrahedron Letters, vol. 38, No. 15, Apr. 14, 1997, pp. 2759–2762.

Takehiro Kawano, "Probing Significance of Diversity in Sialic Acid—Biochemical Approach—",Bio Industry, vol. 14, No. 8, pp. 22–30 (1997).

Kosei Takeuchu and Naoki Takahashi, "Role of Cell Adhesion Molecules as Signal Transducers, and as Downstream Targets of Hox Genes", vol. 16, No. 6, pp. 801–812 (1997).

A. Kobayashi et al., "Receptor–mediated regulation of differentiation and proliferation of hepatocytes by synthetic polymer model of asialogylcoprotein", J. Biomater. Sci. Polymer Edn., vol. 6, No. 4, pp. 325–342 (1994).

M. Goto et al., "Lactose–carrying polystyrene as a drug carrier: investigation of body distributions to parenchymal liver cells using $^{125}$ I–labelled lactose–carrying polystyrene", Journal of Controlled Release, 28, pp. 223–233 (1994).

L. Shapiro et al., "Novel alginate sponges for cell culture and transplantation", Biomaterials, 18, pp. 583–590 (1997).

J. Glass et al., "Characterization of a hyaluronic acid–Arg––Gly–Asp peptide cell attachment matrix", Biomaterials, 17, pp. 1101–1108 (1996).

* cited by examiner

*Primary Examiner*—David M. Naff
(74) *Attorney, Agent, or Firm*—Wenderoth, Lind & Ponack, L.L.P.

(57) ABSTRACT

A cell culture material comprising a sugar containing polymer in which at least one kind of sugar chain is bonded as a side chain via a spacer molecule is made into a three-dimensional shape whereupon a three-dimensional cell material is prepared. With regard to the sugar containing polymer, a sugar containing polymer having a carboxyl group such as alginic acid, hyaluronic acid, pectic acid or a derivative thereof is preferably used. Sugar chain having a specific recognition to a cell is bonded as a side chain and, therefore, when the cell is incubated using the cell culture material, it is possible to maintain and improve the proliferation, morphology and function of the cells and to retain the cell form in a form of near that in vivo due to a specific interaction between the cell and the sugar chain.

16 Claims, 2 Drawing Sheets

THREE-DIMENSIONAL CELL CULTURE MATERIAL HAVING SUGAR POLYMER CONTAINING CELL RECOGNITION SUGAR CHAIN

This application is a 371 of PCT/JP99/06248 filed Nov. 10, 1999.

BACKGROUND OF THE INVENTION

1. Field of the Invention

The present invention relates to a three-dimensional cell culture material made into a three-dimensional shape whereby proliferation, morphology and function of cells can be expressed in the same manner as in the cells in vivo and also to a method for the incubation of cells using the cell culture material.

2. Description of the Related Art

Progress in glyco-engineering in recent years is remarkable. For example, proteoglycan, glycolipid, glycoprotein, etc. in cell walls of vegetable cells are exemplified as biopolymers having sugar chains. Each of them is believed to participate in (1) stabilization of cells, (2) differentiation, proliferation, adhesion and migration of cells and (3) interaction among the cells and cell recognition and various reports have been available. In addition, a mechanism where the sugar chains of those polymers act for another, assist, amplify, adjust or inhibit their functions of each other whereby they control high and precise bioreactions has been gradually clarified.

Further, such sugar chains differentiate and proliferate the cells and participate in adhesion of cells and their relation with immune and malignant alteration of cells has been made clear. Thus, development of various industries can be expected by attempting a new development by a close connection of the glyco-engineering with medicine, cell engineering or tissue engineering.

An example is that there have been brisk studies for onset of diseases due to abnormal interaction among sugar chains on cell surfaces and among sugar chain receptors or for role of sugar chain in viral infection such as AIDS (Takehiro Kawano, *Bio Industry*, 14, 22–30(1997)). In addition, studies on protein which recognizes the sugar chain such as secretin, contactin and contactinhibin as a molecule for mediating the adhesion between cells have become important in understanding the bioreactions (Tuneshige Takeuchi and Naoki Takahashi, *Saibo Kogaku*, 16, 801–812(1997)).

The present inventors already carried out an intensive investigation paying their attention to a cell-specific interaction of sugar chain and, as a model for ligand against asialoglycoprotein receptors, they designed and synthesized poly(N-p-vinylbenzyl-[O-β-D-galactopyranosyl-(1→4)-D-gluconamide]) (abbreviated as PVLA) which was a polystyrene having galactose in a side chain. For example, in a hepatocyte incubation experiment on a culture dish coated with this PVLA as a cell culture material, it was found that parenchymal hepatocytes are selectively incubated via a specific affinity of PVLA with asialoglycoprotein receptor on the surface of parenchymal hepatocytes and that, even under a two-dimensional culture material environment, parenchymal hepatocytes per se were made into a three-dimensional shape and specifically existed as spheroids (A. Kobayashi, M. Goto, K. Kobayashi, T. Akaike, J. Biomater. *Sci. Polymer Edn.*, 6, 325–342 (1994)). However, this PVLA has a structure having polystyrene which is a synthetic polymer as a main chain and, therefore, it has disadvantages that no biodegradability is available and there are possibilities of expression of antigenicity and of having a toxicity.

In the meanwhile, incubation of cells using a culture dish coated with an adhesion protein such as collagen, fibronectin or laminin which is a natural protein has been also carried out. However, that is a two-dimensional culture and, therefore, proliferation of cells, expression of cell functions, etc. are not sufficiently achieved.

Recently, there has been an attempt where natural or synthetic polymer such as collagen, alginic acid, hyaluronic acid and polyisopropylacrylamide is cross-linked using ultraviolet ray, radioactive ray or chemical cross-linking agent to give a culture material in a three-dimensional form and cells are incubated using the same. However, there are problems that cell adhesion is not good whereby proliferation of the cells is often suppressed, cell function lowers, cell form is extended unlike that in vivo, etc. and no system for a good incubation of cells has been available.

SUMMARY OF THE INVENTION

An object of the present invention is therefore to provide a three-dimensional cell culture material made into a three-dimensional form whereby adhesion and proliferation of cells are promoted, cell functions are maintained and improved and the cell form can be retained in a form near that in vivo, and also to provide a method for the incubation of cells using the three-dimensional cell culture material.

Thus, the present invention is a three-dimensional cell culture material, characterized in that a cell culture material comprising a sugar containing polymer in which at least one kind of sugar chain is bonded as a side chain via a spacer molecule is made into a three-dimensional shape.

Further, the present invention is a method for the incubation of cells, characterized in that, cells are incubated using the three-dimensional cell culture material whereby proliferation, morphology and function of the cells are maintained and improved.

DESCRIPTION OF THE PREFERRED EMBODIMENTS

Figure 1:
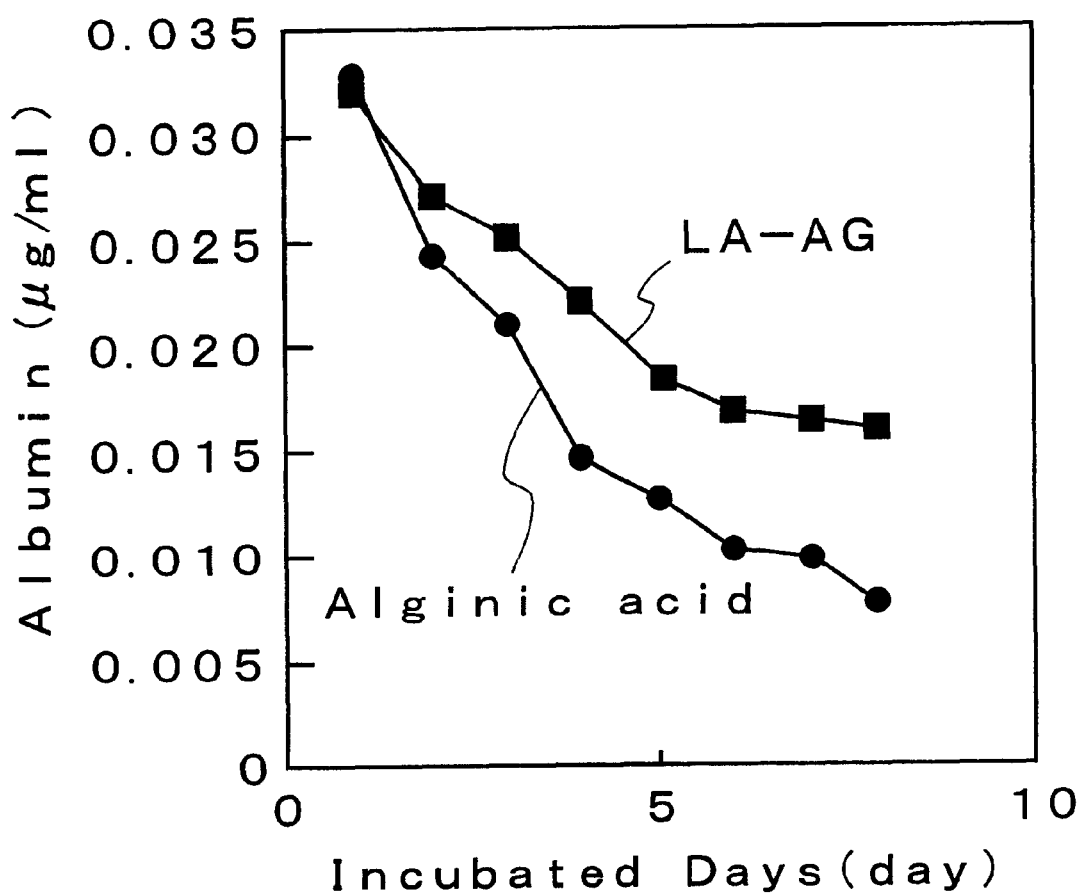
FIG. 1 is a graph showing the relation between the production amount of albumin from parenchymal hepatocytes and the incubated days where gel beads of LA-AG and of alginic acid only are used.

The three-dimensional cell culture material of the present invention is that a sugar containing polymer (i.e. a polymer containing sugar chain) is a main chain and a sugar chain is bonded to the main chain as a side chain via a spacer molecule. The general structural formula when a diamine is used as a spacer molecule is shown in the formula (1).

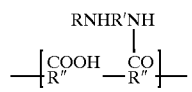
(1)

In the above formula (1), the moiety in the brackets is a sugar containing polymer and sugar containing polymers having a carboxyl group such as alginic acid, hyaluronic acid, pectic acid or derivatives thereof are preferably used. With regard to pectic acid, pectin where pectic acid is a main component may be used as well. Although various other sugar containing polymers than the above may be also used in the present invention so far as they are able to introduce the sugar chain as a side chain, the above-exemplified sugar containing polymers are widely used as the materials for food, cosmetics, etc. and their affinity to cells is good whereby they are particularly preferred. With regard to the molecular weight of the sugar containing polymer, that of around 30,000–200,000 may be preferably used. When the molecular weight is too low, a sol state is resulted and, therefore, there is a tendency that a three-dimensional shape is hardly formed.

R in the above formula (1) is a sugar chain bonded to the sugar containing polymer as a side chain. As to the sugar chain in the present invention, anything may be used so far as it is able to hold a sugar residue which interacts with the cells under a state of being bonded to the sugar containing polymer as a side chain and its examples are monosaccharide and oligosaccharide such as glucose, glactose, mannose, N-acetylglucosamine, N-acetylgalactosamine, lactose, maltose, laminalibiose, chitobiose, maltobiose, uronic acid-related substances, sulfated sugars, etc.

Bonding between the sugar containing polymer and the sugar chain is carried out via a spacer molecule. With regard to the spacer, a diamine having two amino groups in a molecule as shown in the above formula (1) may be preferably used. Thus, an amide bond is formed between one of the amino groups in the diamine and a terminal carboxyl group of the lactonated sugar chain while another amide bond is formed between another amino group in the diamine and the carboxyl group in the sugar containing polymer whereby the sugar chain can be effectively and easily introduced into the sugar containing polymer. R' in the spacer molecule in the formula (1) is an alkyl group, a benzene ring, etc. and examples of the diamine are ethylenediamine, hexaethylenediamine, diaminoxylene, etc. Besides the diamine, a compound having two functional groups in a molecule such as aminoethanol may also be used as a spacer molecule. In the case of aminoethanol, an amino group and a hydroxyl group in the molecule are able to bond the sugar containing polymer to the sugar chain by means of an amide bond and an ester bond, respectively. Alternatively, a sugar containing polymer into which a spacer molecule is previously introduced can be bonded to the sugar chain or the sugar chain into which a spacer molecule is previously introduced can be bonded to the sugar containing polymer. However, when the sugar chain is able to be directly introduced into the carboxyl group of the sugar containing polymer, the space molecule is not always necessary.

Although the amount of the sugar chain to be introduced into the sugar containing polymer is not particularly limited, it is preferred to introduce the sugar chain in around 10–50% of the numbers of the carboxyl group in the sugar containing polymer. The sugar chain to be introduced into the sugar containing polymer may be one kind or two or more kinds of sugar chains may be introduced. Cells have their own specific sugar chain recognition ability and, therefore, when a sugar containing polymer into which two or more kinds of sugar chains having different recognizing properties by cells are introduced is used as a culture material, it is possible to freely control proliferation, morphology and function of the cells by controlling the type of the sugar chains to be combined and their introducing rate.

When two or more kinds of sugar chains are bonded to the sugar containing polymer, it is possible that the sugar chains of different kinds are bonded to the sugar containing polymer at the same time or it is also possible that, after one kind of sugar chain is bonded to the sugar containing polymer, another sugar chain is successively bonded to the sugar containing polymer.

Specific examples of the sugar containing polymer into which a sugar chain is introduced as a side chain will be described hereinbelow by showing the structural formulae. Incidentally, the bonding of the sugar chain to the sugar containing polymer is a reaction of polymer with a low-molecular substance and, therefore, it takes place randomly and the bonding is not always limited to the bonding position as shown in the formulae.

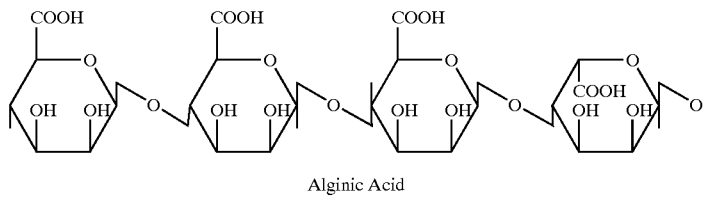

Alginic Acid

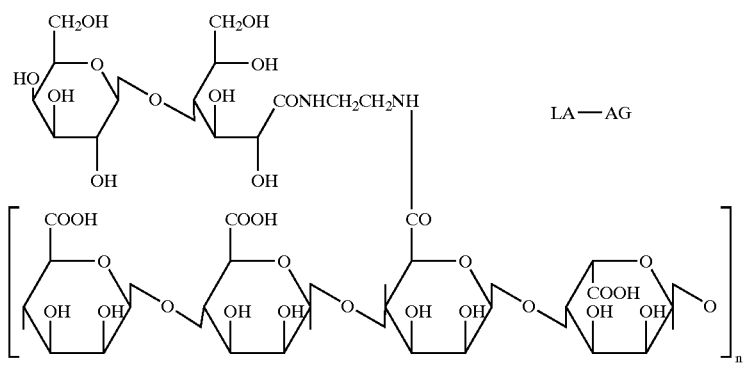

1-N-[O-β-D-Galactopyranosyl-(1–4)-D-gluconamide] methyl-2-N'-methylamide alginate represented by the above formula (2) (hereinafter, abbreviated as LA-AG) is a compound in which lactobionic acid is bonded to one of the amino groups of ethylendiamine while another amino group is bonded to a carboxylic group of alginic acid.

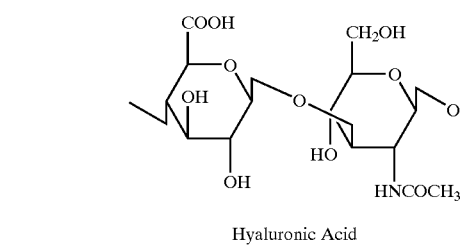

Hyaluronic Acid

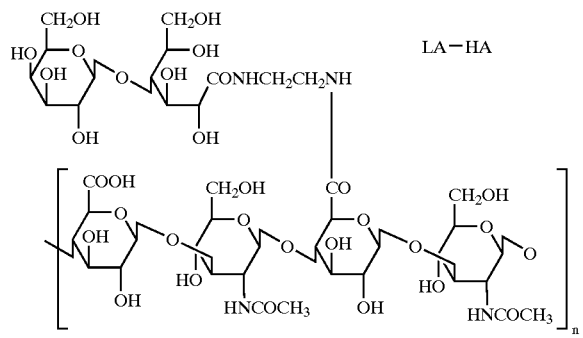

1-N-[O-β-D-Galactopyranosyl-(1→4)-D-gluconamide] methyl-2-N'-methylamide hyaluronate represented by the above formula (3) (hereinafter, abbreviated as LA-HA) is a compound in which lactobionic acid is bonded to one of the amino groups of ethylendimaine while another amino group is bonded to a carboxyl group of hyaluronic acid.

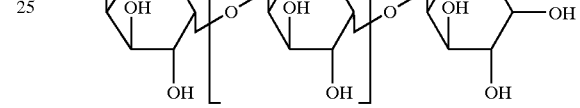

Pectic Acid

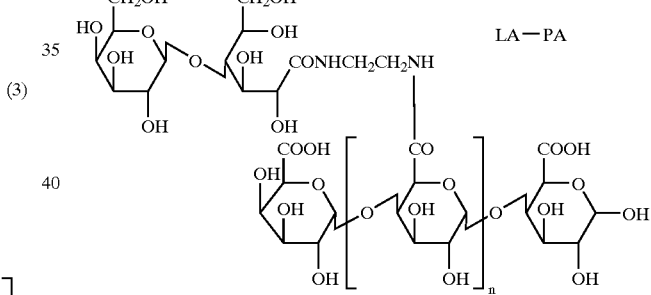

1-N-[O-β-D-Galactopyranosyl-(1→4)-D-gluconamide] methyl-2-N'-methylamide pectinate (hereinafter, abbreviated as LA-PA) represented by the above formula (4) is a compound in which lactobionic acid is bonded to one of the amino groups of ethylenediamine while another amino group is bonded to a carboxylic group of pectic acid.

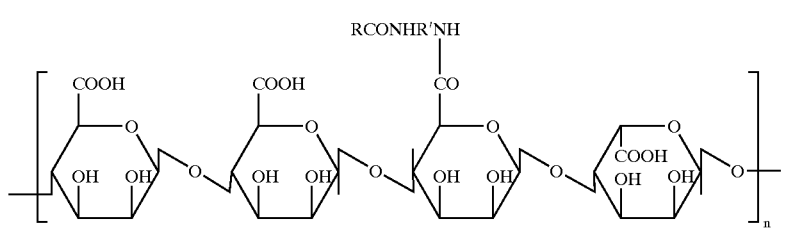

The compound represented by the above formula (5) is a compound in which any sugar chain R is bonded to one of amino groups of any spacer compound while another amino group is bonded to a carboxyl group of alginic acid.

(6)

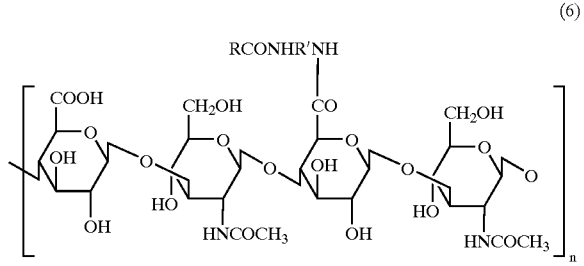

The compound represented by the above formula (6) is a compound in which any sugar chain R is bonded to one of amino groups of any spacer compound while another amino group is bonded to a carboxyl group of hyaluronic acid.

(7)

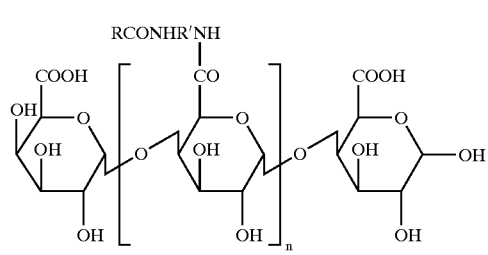

The compound represented by the above formula (7) is a compound in which any sugar chain R is bonded to one of amino groups of any spacer compound while another amino group is bonded to a carboxyl group of pectic acid.

In the present invention, a cell culture material comprising the above-mentioned sugar containing polymer to which a sugar chain is bonded as a side chain is made into a three-dimensional shape whereupon a three-dimensional cell culture material is prepared. As to a method for making into a three-dimensional shape, known methods described in various literatures as the methods for the shape-formation of common sugar containing polymers (sugar containing polymers where sugar chain is not bonded as a side chain) may be adopted.

For example, in the case of a culture material in which alginic acid is a sugar containing polymer, calcium is added to a solution of this culture material whereupon beads in a form of gel comprising a complex of the culture material with calcium can be prepared. Further, in the case of a culture material in which hyaluronic acid is a sugar containing polymer, a concentrated solution of the culture material is treated with ultraviolet ray, radioactive ray, a chemical cross-linking agent, etc. to cross-link the hyaluronic acid followed by freeze-drying or, cross-linked after freeze-drying whereupon a sponge of the culture material can be prepared. Furthermore, when a solution of a culture material in which alginic acid is a sugar containing polymer is mixed with a calcium solution to homogenize followed by freeze-drying, a sponge can be prepared.

It is also possible that a culture material is carried on a carrier such as polystyrene by means of a physico-chemical method such as adsorption or by means of a chemical method such as a covalent bond to form into a three-dimensional shape.

In the formation of the cell culture material into a three-dimensional shape, it is further possible that a mixture comprising a sugar containing polymer in which sugar chain is bonded as a side chain and a common sugar containing polymer (a sugar containing polymer in which no sugar chain is bonded as a side chain) is shaped as such.

In carrying out the cell incubation using the above-mentioned three-dimensional cell culture material of the present invention, the cell incubating methods which have been commonly used up to now may be adopted as they are. For example, in the case where a three-dimensional cell culture material comprising the beads in a gel form is used, a cell suspension is mixed with a solution of the cell culture material and calcium is added thereto to shape into beads whereupon gel beads wherein the cell are involved can be prepared and the beads may be incubated in a liquid medium.

It is also possible that a cell suspension is sown on a previously-prepared sponge-shaped three-dimensional cell culture material so that the cells are introduced and involved in the sponge followed by incubating by a conventional method.

When the cells are incubated as such, it is possible that, due to a specific sugar chain recognition of the cells, adhesion and proliferation of the cells are promoted, cell functions are maintained and improved and the cell form is held in a form similar to that in vivo.

In the above-mentioned cell incubation, only one kind of the three-dimensional cell culture material according to the present invention may be used or two or more kinds thereof may be mixed and used. In addition, not only the three-dimensional culture material of the present invention but also the three-dimensional cell culture material of the present invention which is combined, if necessary, with sugar containing polymer, adhesion protein such as collagen, various natural polymer, etc. may be subjected to a cell incubation.

EXAMPLE 1

Synthesis of LA-AG (Formula (1))

(a) Synthesis of 1-N-[O-β-D-galactopyranosyl-(1→4)-D-gluconamide]methyl-2-N'-methylamine (Hereinafter, Abbreviated as LA-ED)

LA-ED was synthesized according to the following reaction formulae.

Reaction Formulae

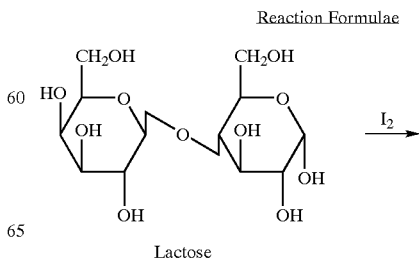

Lactose

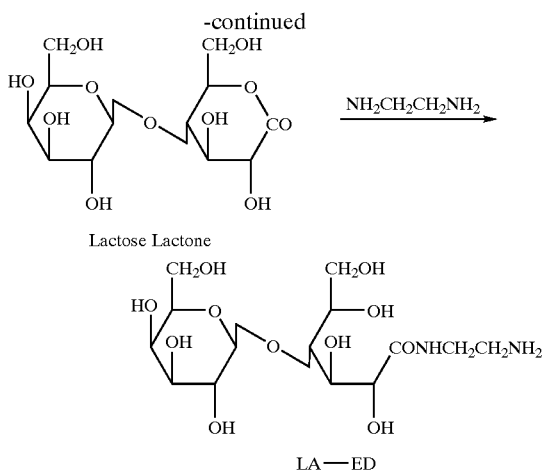

Lactose Lactone

LA—ED

First, lactonization of lactose was carried out by a method mentioned in M. Goto, et al., *J. Controlled Release*, 28, 223–233 (1994). Its summary will be as follows. Namely, a lactose was dispersed in distilled water and diluted with methanol. The diluted dispersion was added to a warmed methanolic solution of iodine, and after stirring, a methanolic solution of potassium hydroxide was gradually added thereto until the color of iodine disappeared. After that, the reaction solution was cooled with ice and the precipitate separated out therefrom was filtered. The precipitate was washed and recrystallized to give a potassium salt of the acid. The resulting potassium salt was passed through an ion-exchange resin to convert to an acid type and methanol was added to the fraction of the acid type followed by concentrating under reduced pressure to give crystals. The operation that the crystals were dissolved in small amount of methanol and the ether was added to precipitate was-repeated for several times and, after that, the precipitate was freeze-dried to give a lactose lactone.

The resulting lactose lactone (5 g) was dissolved in 50 ml of DMSO and 20 g of ethylenediamine were added thereto followed by reacting under refluxing for 4 hours. This was allowed to cool, the precipitate was filtered off, the reaction solution was added to 300 ml of chloroform and the precipitated white crystals were filtered. They were washed with ether and small amount of cold methanol to give 5 g of LA-ED.

(b) Synthesis of LA-AG:

Alginic acid was dissolved in 50 ml of a TEMED buffer (pH 4.7), 0.97 g of a water-soluble carbodiimide (WSC) was added as a condensing agent and the mixture was made to react at room temperature with stirring for one hour. The above-prepared LA-ED (2 g) was added to this solution and the mixture was made to react with stirring at room temperature for 3 days. The solution was dialyzed against 20 liters of pure water and, after completion of the dialysis, a freeze-drying was carried out to give a desired product. From the $^1$H-NMR spectrum of this product, 2.69 ppm of ethylenediamine $CH_2CH_2$, 3.25 ppm of amide NH, 3.5–4.5 ppm of lactose and alginic acid sugar chain were observed and the product was confirmed to be LA-AG. The amount of the sugar chain introduced thereinto was calculated to be about 15%.

EXAMPLE 2

Incubation of Parenchymal Hepatocytes Using LA-AG Beads (a) Collection of Parenchymal Hepatocytes:

Parenchymal hepatocytes were collected and isolated from the liver of mouse according to a method mentioned in the literature (A. Kobayashi, M. Goto, K. Kobayashi, T. Akaike, *J. Biomater. Sci. Polymer Edn.*, 6, 325–342 (1994)). The isolated parenchymal hepatocytes were used by diluting with a Willium's medium E containing 5% of fetal bovine serum.

(b) Preparation of Cell-containing LA-AG Beads:

To a mixed solution of alginic acid (1% w/v) and LA-AG (1% w/v) in an aqueous physiological saline solution were added fetal bovine serum (FCS; 5% v/v), epidermal growth factor (EGF; 20 ng/ml) and insulin (Ins; $10^{-8}$ M) to make each of their concentrations as given in parentheses and then parenchymal hepatocytes were mixed therewith to make the cell concentration 800,000 cell/ml. The cell solution was placed in a syringe and dropped into a 100 mM aqueous solution of calcium chloride using a needle of 26 (G×½") whereupon gel beads were formed. As such, the gel beads having an average particle size of about 3 mm were prepared. The beads were gelled by incubating for 5 minutes or more.

Then, after washing with a CHES buffer (pH 5.0) for several times, washings with a physiological saline solution were carried out for several times more. After that, surfaces of the gel beads were treated with a 0.05% solution of poly-L-lysine in a physiological saline solution for 5 minutes and washed with a physiological saline solution for several times. Then, the surfaces of the gel beads were coated with a 0.15% aqueous solution of alginic acid for 5 minutes followed by washing with a physiological saline solution for several times. The beads were further treated with a 50 mM aqueous solution of sodium citrate for 5 minutes and washed with a physiological saline solution for 3 times to prepare cell-containing LA-AG beads.

Depending upon the content of the sugar chain to be introduced into LA-AG, it is also possible to make into beads where LA-AG and alginic acid are not mixed but only LA-AG is used.

For the sake of comparison, the same operation as mentioned above was carried out except that a physiological saline solution containing 2% w/v alginic acid only was used in place of the above-mentioned mixed solution of alginic acid and LA-AG in a physiological saline solution whereupon the cell-containing alginic acid beads were prepared.

(c) Incubation of Cell-containing LA-AG Beads:

The resulting cell-containing LA-AG beads were incubated in an L15 medium containing FCS (5% v/v), EGF (20 ng/ml) and Ins ($10^{-8}$M) and the function of the parenchymal hepatocytes involved in the beads was evaluated. For the sake of comparison, the same incubation was carried out for the cell-containing alginic acid beads as well and the function of the parenchymal hepatocytes involved in the beads was evaluated.

(e) Evaluation of Function of Parenchymal Hepatocytes:

Function of the parenchymal hepatocytes in the gel beads was evaluated by the amount of albumin produced from the parenchymal hepatocytes. Measurement of albumin was carried out by a common method using a kit (manufactured by Bio-Rad, U.S.A.) for the measurement of albumin.

Result of the measurement of the produced amount of albumin is shown in FIG. 1. In the case of the parenchymal hepatocytes incubated with the LA-AG gel beads, the albumin production amount on the 8th day after the incubation was 0.0158 μg/ml while that incubated with the gel beads of alginic acid only was 0.00765 μg/ml. From the above, it was noted that, in the product incubated with the LA-AG gel beads, function of parenchymal hepatocytes was more maintained and improved.

It was also noted that, in the case where the parenchymal hepatocytes were incubated in the LA-AG gel beads, spheroids comprising several cells were observed from the 3rd day of the incubation whereby migration and proliferation of the cells were promoted.

Figure 2:
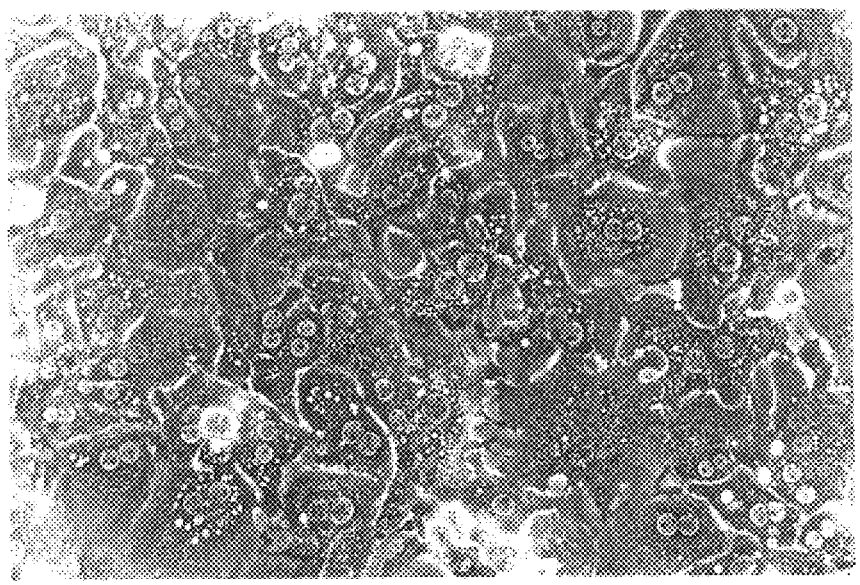
FIG. 2 is a microphotograph showing the morphology of parenchymal hepatocytes incubated on a culture dish coated with collagen.
Figure 3:
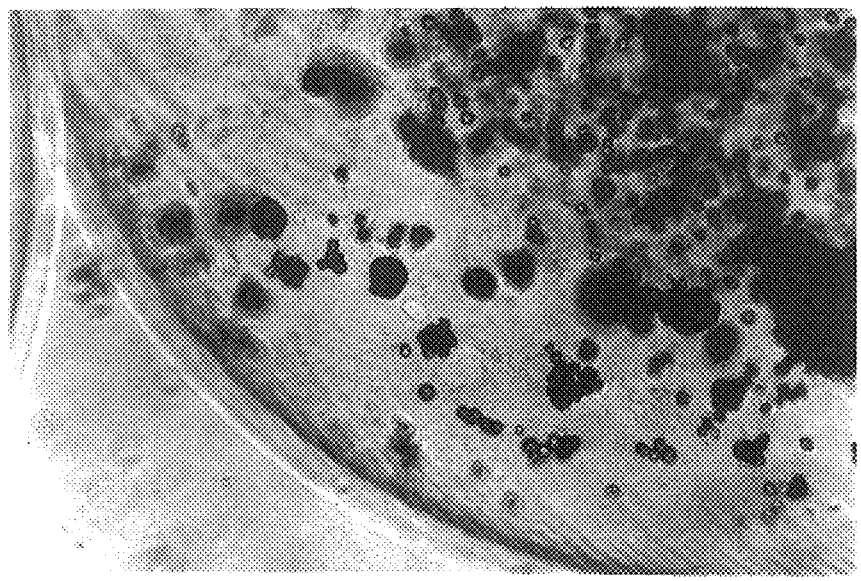
FIG. 3 is a microphotograph showing the morphology of parenchymal hepatocytes incubated using LA-AG gel beads.

It was further clarified that, when an incubation was carried out using the LA-AG gel beads of a three-dimensional shape, a globular form (refer to the microphotograph of FIG. 3) was resulted unlike the extended form (refer to the microphotograph of FIG. 2) observed in the incubation of the parenchymal hepatocytes on a collagen-coated culture dish in a two-dimensional shape. It is noted from the above that, when the parenchymal hepatocytes are incubated in the LA-AG gel beads, the morphology of the parenchymal hepatocytes in vivo can be retained.

EXAMPLE 3

Incubation of Parenchymal Hepatocytes Using LA-AG Sponge (a) Preparation of LA-AG Sponge:

This was carried out according to a method mentioned in the literature (L. Shapio, S. Cohen, Biomaterials, 18, 583–590 (1997)). Namely, 1 ml of a mixed aqueous solution of LA-AG (1% v/v) and alginic acid (1% w/v) was added to a 24-hole multi-plate and then a 0.01% (w/v) aqueous solution of calcium chloride in the same amount was gradually added thereto. This was mixed for 3 minutes using a homogenizer (6G, 31,800 rpm), frozen in a freezer of $-18°$ C. and then freeze-dried to give an LA-AG sponge.

For the sake of comparison, the same operation as above was carried out using an aqueous solution of only alginic acid (2% w/v) in place of the mixed aqueous solution of LA-AG and alginic acid to prepare an alginic acid sponge.

(b) Incubation of Parenchymal Hepatocytes on Sponge:

Parenchymal hepatocytes of mouse were collected and isolated by a method mentioned in Example 2, the cells were added to a Willium's medium E containing FCS (5% v/v), EGF (20 ng/ml) and Ins ($10^{-8}$ M) and sown on the sponge so as to make the cell concentration 800,000 cells/ml. The sponge was incubated for a predetermined period and the function of the parenchymal hepatocytes incubated on the sponge was evaluated by measuring the production amount of albumin.

The parenchymal hepatocytes incubated on the LA-AG sponge produced 0.0144 μg/ml of albumin on the 8th day of the incubation while, in the sponge solely comprising alginic acid, the production was 0.00544 μg/ml.

EXAMPLE 4

Incubation of Parenchymal Hepatocytes Using LA-HA Sponge (a) Synthesis of LA-HA:

This was carried out according to the method for the synthesis of LA-AG in Example 1. Namely, hyaluronic acid was dissolved in 50 ml of a TEMED buffer (pH 4.7), 0.97 g of WSC was added as a condensing agent and the mixture was made to react by stirring at room temperature for 1 hour. To this solution were added 2 g of LA-ED obtained in Example 1 and the reaction was carried out with stirring at room temperature for 3 days. The solution was dialyzed against 20 liters of pure water and, after completion of the dialysis, a freeze-drying was carried out to give a desired product. From a $^1$H-NMR spectrum of the product, there were observed 2.0 ppm of hyaluronic acid $CH_3$, 3.30 ppm of amide NH, 3.3–4.6 ppm of lactose and alginic acid sugar chain whereby the product was confirmed to be LA-HA. The amount of the sugar chain introduced thereinto was calculated as about 13%.

(b) Preparation of LA-HA:

This was carried out according to a method mentioned in the literature (J. R. Glass, et al., Biomaterials, 17, 1101–1108 (1997)). Namely, LA-HA (1% w/v) and hyaluronic acid (1% w/v) were mixed and dispersed in a 0.5% aqueous solution of sodium hydroxide. To the dispersion was added 0.5 μl of 1,4-butanediethanol diglycidyl ether (a cross-linking agent) and the reaction was carried out for 16 hours. After dialyzing the reaction solution, it was frozen using a freezer of $-20°$ C. and then freeze-dried to prepare an LA-HA sponge.

For the sake of comparison, the same operation as above was carried out using hyaluronic acid only in place of LA-HA and hyaluronic acid to prepare a hyaluronic acid sponge.

(c) Incubation of Parenchymal Hepatocytes on Sponge:

Parenchymal hepatocytes of mouse were collected and isolated by the method mentioned in Example 2, the cells were added to a Willium's medium E containing FCS (5% v/v), EGF (20 ng/ml) and Ins ($10^{-8}$ M) and sown on the sponge to make the cell concentration 800,000 cells/ml. The sponge was incubated for a predetermined period and the function of the parenchymal hepatocytes incubated on the sponge was evaluated by measuring the amount of albumin produced.

The parenchymal hepatocytes incubated on the LA-HA sponge produced 0.0166 μg/ml of albumin on the 8th day of the incubation while, in the case of the sponge of hyaluronic acid only, the amount was 0.00483 μg/ml.

Since the three-dimensional cell culture material of the present invention comprises a sugar containing polymer in which sugar chain having a specific recognition to cell is bonded as a side chain, it is possible by incubating the cells using such a cell culture material that, due to a specific interaction between cell and sugar chain, adhesion and proliferation of the cell are promoted, cell function is maintained and improved and the cell form is kept in a form which is similar to that in vivo. Accordingly, it is possible to prepare the cell of any form retaining the same proliferation and function as those in vivo and, for example, it is possible to apply the thus-prepared cells to a hybrid artificial liver.

Further, like the sugar containing polymer having no sugar chain such as alginic acid and hyaluronic acid, the cell culture material of the present invention is easily able to give a three-dimensional shape. Especially when a sugar containing polymer comprising alginic acid, hyaluronic acid, pectin or derivatives thereof is used, the sugar chain can be easily introduced as a side chain and, since the manufacturing cost is also relatively low, it is possible to prepare a disposable product.

What is claimed is:

1. A three-dimensional cell culture material comprising a cell culture material having (1) a three-dimensional shape, and
   (2) a sugar containing polymer as a main chain, wherein said sugar containing polymer comprises at least one kind of sugar chain having a specific recognition to a cell, and a spacer molecule which is a diamine having a first and a second amino group therein to bond said sugar chain to said sugar containing polymer as a side chain,
   (3) wherein the first amino group of the diamine is directly bonded to the sugar chain, and the second amino group of the diamine is directly bonded to the sugar of the sugar containing polymer.

2. The three-dimensional cell culture material according to claim 1, wherein the sugar containing polymer is a sugar containing polymer comprising a carboxyl group or a derivative of said sugar containing polymer comprising said carboxyl group.

3. The three-dimensional cell culture material according to claim 2, wherein the sugar containing polymer is alginic acid or a derivative thereof.

4. The three-dimensional cell culture material according to claim 2, wherein the sugar containing polymer is hyaluronic acid or a derivative thereof.

5. The three-dimensional cell culture material according to claim 2, wherein the sugar containing polymer is pectic acid or a derivative thereof.

6. The three-dimensional cell culture material according to claim 1, wherein the sugar containing polymer comprises two or more kinds of sugar chains bonded as side chains.

7. A method for incubating cells comprising introducing cells into the three-dimensional cell culture material according to claim 1, and incubating said cells to maintain and improve the proliferation, morphology and function of said cells.

8. A method for incubating cells comprising introducing cells into a mixture of two or more different three-dimensional cell culture materials according to claim 1, and incubating said cells to maintain and improve the proliferation, morphology and function of said cells.

9. A three-dimensional cell culture material comprising a cell culture material having (1) a three-dimensional shape, and
   (2) a sugar containing polymer as a main chain, wherein said sugar containing polymer is a mixture of (a) a sugar containing polymer comprising at least one kind of sugar chain having a specific recognition to a cell, and a spacer molecule which is a diamine having a first and a second amino group therein to bond said sugar chain to said sugar containing polymer as a side chain, and (b) a sugar containing polymer in which no sugar chain is bonded as a side chain,
   (3) wherein the first amino group of the diamine is directly bonded to the sugar chain, and the second amino group of the diamine is directly bonded to the sugar of the sugar containing polymer.

10. The three-dimensional cell culture material according to claim 9, wherein the sugar containing polymer is a sugar containing polymer comprising a carboxyl group or a derivative of said sugar containing polymer comprising said carboxyl group.

11. The three-dimensional cell culture material according to claim 10, wherein the sugar containing polymer is alginic acid or a derivative thereof.

12. The three-dimensional cell culture material according to claim 10, wherein the sugar containing polymer is hyaluronic acid or a derivative thereof.

13. The three-dimensional cell culture material according to claim 10, wherein the sugar containing polymer is pectic acid or a derivative thereof.

14. The three-dimensional cell culture material according to claim 9, wherein the sugar containing polymer comprises two or more kinds of sugar chains bonded as side chains.

15. A method for incubating cells comprising introducing cells into the three-dimensional cell culture material according to claim 9, and incubating said cells to maintain and improve the proliferation, morphology and function of said cells.

16. A method for incubating cells comprising introducing cells into a mixture of two or more different three-dimensional cell culture materials according to claim 9, and incubating said cells to maintain and improve the proliferation, morphology and function of said cells.

* * * * *